United States Patent [19]

Halle et al.

[11] 4,302,569
[45] Nov. 24, 1981

[54] 2-CHLORO-2-ALKYL SUBSTITUTED PEROXYESTERS

[75] Inventors: Reidar Halle, Novato; David Peterson, Hercules, both of Calif.

[73] Assignee: Argus Chemical Corporation, Brooklyn, N.Y.

[21] Appl. No.: 203,788

[22] Filed: Nov. 3, 1980

Related U.S. Application Data

[60] Division of Ser. No. 98,010, Nov. 28, 1979, Pat. No. 4,278,612, which is a continuation-in-part of Ser. No. 50,898, Jun. 21, 1979, abandoned.

[51] Int. Cl.$^3$ .............................. C08F 4/34; C08F 4/36
[52] U.S. Cl. .............................. 526/231; 260/453 RZ; 525/27
[58] Field of Search ........................................ 526/231

[56] References Cited

FOREIGN PATENT DOCUMENTS 534709 12/1956 Canada .

*Primary Examiner*—Stanford M. Levin
*Attorney, Agent, or Firm*—Townsend and Townsend

[57] ABSTRACT

Novel mono and di peroxyesters characterized by chloro-substitution of a tertiary carbon atom at the alpha position relative to the carbonyl group(s), the monoperoxyesters having no less than 9 carbon atoms and the diperoxyesters having no less than 16 carbon atoms, are utilized as polymerization initiators. Typical is the polymerization of styrene and the copolymerization of vinyl chloride and vinyl acetate.

22 Claims, No Drawings

2-CHLORO-2-ALKYL SUBSTITUTED PEROXYESTERS

This is a division of application Ser. No. 98,010 filed Nov. 28, 1979, now U.S. Pat. No. 4,278,612, which in turn is a continuation-in-part of U.S. patent application Ser. No. 50,898 filed June 21, 1979, abandoned.

BACKGROUND OF THE INVENTION

1. Field of the Invention:

This invention relates to polymerization using a peroxyester as the initiator. More particularly, it relates to certain mono and di peroxyesters having a chlorine and an alkyl substituent on the carbon atom in the alpha position relative to the carbonyl group and their use as initiators for the polymerization and copolymerization of monomers, such as ethylene, styrene, methyl methacrylate and vinyl chloride and including copolymerizations of the like with other monomers such as vinyl acetate.

2. Brief Description of the Prior Art:

U.S. Pat. Nos. 3,264,274 and 3,444,230 describe non-halo substituted diperesters and acetylenic diperesters, respectively.

U.S. Pat. Nos. 2,865,904 and 3,089,865 describe halogenated acyl peroxides.

Alpha-halo-substituted diacyl peroxides are disclosed in U.S. Pat. Nos. 3,652,631 and 4,032,605.

Alpha-halo-substituted mono and di peroxyesters wherein the alpha carbon relative to the carbonyl is always a secondary carbon atom are disclosed in U.S. Pat. No. 4,051,167.

t-Butyl peroxy 2-chloro-2-methyl propionate is disclosed in Chem. Br. 104, 593–604 (1971).

Zh. Org. Khim. 6, 466 (1970) discloses the symmetrical diacyl peroxide di (2-chloro-2-methyl) propionyl peroxide and benzoyl 2-chloro-2-methyl propionyl peroxide.

SUMMARY OF THE INVENTION

Novel peroxyesters are provided which are aliphatic monoperoxyesters or diperoxyesters having a chlorine substituted tertiary carbon atom in the alpha position relative to the carbonyl group(s).

The peroxyesters of the present invention are homologous to t-butyl 2-chloro-2-methyl propionate but have longer aliphatic chains attached to the carbon atom in the alpha position relative to the carbonyl groups and are usually formed from higher molecular weight acid chlorides. The new peroxyesters are surprisingly more efficient initiators for the polymerization of ethylenically unsaturated monomers, such as ethylene, styrene and methyl methacrylate and for copolymerizations such as that of vinyl chloride and vinyl acetate.

DESCRIPTION OF THE SPECIFIC EMBODIMENT

The peroxyesters of the present invention are organic peroxides of the formula:

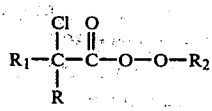

wherein $R_2$ is selected from the group consisting of:

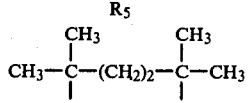

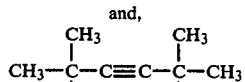

and $R$ and $R_1$ are straight or branched alkyl groups, preferably straight chain, which collectively contain from 2 to about 10, preferably 2 to 7, carbon atoms, providing $R$ and $R_1$ are not both methyl when $R_2$ is t-butyl;

$R'$ and $R_1'$ are straight or branched chain alkyl groups, preferably straight chain, which collectively contain from 2 to about 10, preferably 2 to 7, carbon atoms;

$R''$ and $R_1''$ are straight or branched chain alkyl groups, preferably straight chain, which collectively contain from 2 to about 10, preferably 2 to 7, carbon atoms; and $R_3$, $R_4$ and $R_5$ are alkyl groups which collectively contain from 3 to about 9, preferably 3 to 6, carbon atoms.

where $R_2$ is

i.e., a tertiary alkyl, the present peroxyesters are monoperoxyesters. Such compounds will have at least 9 carbon atoms, no more than about 22 carbon atoms, and will be 2-chloro, 2-alkyl-disubstituted peroxyesters.

Alternatively where $R_2$ is not (a) above, but is selected from (b) or (c) above, the molecules of the present invention are diperoxyesters, including acetylenic diperoxyesters. Typically such diperoxyesters will have from about 16 to about 32 carbon atoms and may be symmetrical or asymmetrical.

The compounds of this invention are readily prepared by conventional methods. Both the mono and di peroxyesters of the present invention are suitably obtained by a conventional base-catalyzed reaction between one or two moles, respectively, of a selected acid chloride and a selected monohydroperoxide or dihydroperoxide in accordance with the following equation (1) for the monoperoxyester and equation (2) for the diperoxyester:

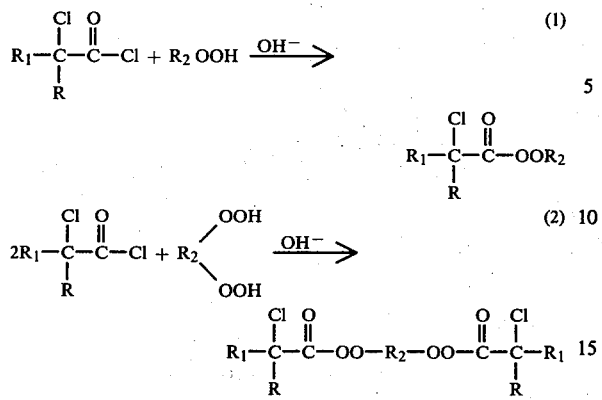

wherein R, $R_1$ and $R_2$ are as described previously.

The above equation (2) for preparing the diperoxyester illustrates a symmetrical product formed from the same acid chloride. Mixed diperoxyesters can be formed using two different acid chlorides for reaction with the two hyrdroperoxide sites on $R_2$.

The acid chlorides are prepared by conventional methods such as that disclosed in J. Organic Chem. 40, 3420 (1975) whereby acids are 2-chlorinated and converted to acid chlorides in one pot.

The following examples will illustrate the synthesis of the peroxyesters of the present invention and their utility as initiators of vinyl chloride and as catalysts of unsaturated polyester resins. For comparison, the present peroxyesters were tested against t-butyl peroxy 2-chloro-2-methyl propionate (TBPCMPr). This comparative prior art peroxyester was selected because it represents the next smallest possible homolog of peroxyesters wherein the alpha carbon is a chloro-substituted tertiary carbon atom.

These examples are provided by way of illustration and not limitation. As will be obvious and understood, other compounds within the scope of this invention may be formed by selecting appropriate reactants and quantities:

EXAMPLE 1

Typical Experimental Procedure: Preparation of 2-chloro-2-ethylhexanoyl chloride To 100 gm of 2-ethylhexanoic acid (0.693 moles) was added 247.5 g of thionyl chloride (2.080 moles) over 30 min. The solution was then heated at 70° for 2 hours. To the cooled solution was added 185.2 gm of N-chloro succinimide (1.387 moles), 165.0 g of thionyl chloride (1.387 moles) and 2.0 ml of concentrated HCl. The mixture was heated at 80° for 2 hours, after which time there was no more apparent $Cl_2$ gas being given off. The mixture was cooled and filtered. The filtrate was distilled at atmospheric pressure to remove the $SOCl_2$ and then distilled to give a major fraction at 95°–105° C. (20 mm) weighing 28.00 gm. Purity was determined by GLC analysis. Purity (area %) was 85.7%; yield was 17.6%. NMR showed no detectable extra chlorination.

GLC analysis was done on a Hewett-Packard 5830A Gas Chromatograph under the following conditions: ⅛"×6" ss column containing 10% DC200 on 80/100 Varaport 30; temperature 1=125° C., time 1–5, rate—15; temperature 2=20° C.; injector temperature=200° C.; FID temperature=250° C.; chart speed=1; and flow rate=30 cc/min.

Utilizing the procedure of Example 1 the 2-chloro-2-alkyl-substituted alkyl chlorides in Table I have been prepared:

TABLE I

| Acid Chloride | % Wt. Purity (Area by GLC) | % Yield |
|---|---|---|
| 1. 2-Chloro-2-ethyl butyryl chloride | 96.5 | 46.4 |
| 2. 2-Chloro-2-methyl pentanoyl chloride | 93.2 | 20.1 |
| 3. 2-Chloro-2-methyl propionyl chloride | 92.5 | 10.9 |

EXAMPLE 2

Typical Experimental Procedure:
1,1,3,3-Tetramethylbutylperoxy-2-chloro-2-ethylbutyrate To 37.61 gm of 4% KOH (0.316 moles) and 30 gm of $H_2O$ at 5° was added 40.00 gm of 83% diisobutylene hydroperoxide (0.227 moles) over 30 min. The mixture was stirred for 10 min., and then 35.57 gm of 96.4% 2-chloro-2-ethylbutyryl chloride (0.210 moles) was added over 1 hour while maintaining the temperature below 10°. The mixture was stirred for another hour at 5° and then partitioned between 50 ml of saturated $NaHCO_3$ solution and 100 ml of petroleum ether. The organic layer was then washed with 100 ml of saturated $NaHCO_3$ solution, dried over anhydrous $MgSO_4$ and evaporated to leave a product weighing 54.83 gm. Product A.O. analysis: theory, 5.74; found, 5.40; 94.2% pure; 88.0% yield.

The following synthesis is a typical method for preparing the diperoxyesters of this invention:

EXAMPLE 3

2,5-dimethyl-2,5-di(2-chloro-2-methylpropionyl peroxy) hexyne-3 (DM-DCMPrH)

To 36.82 gm of 47% KOH (0.309 moles) and 70 gm of $H_2O$ at 5° C. was added 23.93 gm of 75% 2,5-dimethyl-2,5-dihydroperoxy hexyne-3 (0.103 moles) over 30 minutes. The mixture was stirred for 15 minutes, and then 30.50 gm of 92% 2-chloro-2-methylpropionyl chloride (0.216 moles) was added over 1 hour while maintaining the temperature below 10° C. The mixture was stirred for another 20 minutes at 7° C. and then partitioned with the addition of 80 ml of petroleum ether. The organic layer was washed twice with 80 ml of saturated $NaHCO_3$ solution, dried over $MgSO_4$ and evaporated to leave the product weighing 30.05 gm. Product A.O. analysis: Theory 8.35; found 7.50; 89.9% pure; 68.4% yield. The I.R. was satisfactory.

Utilizing the procedure of Examples 2 and 3 the peroxyesters in Table II were prepared:

TABLE II

RESULTS OF THE SYNTHESIS OF VARIOUS 2-CHLORO-2-ALKYL SUBSTITUTED PEROXYESTERS

| PEROXYESTER | MW | TAO | A.O. | % WT. PURITY | YIELD WT,g/THEORY WT,g | % WT YIELD |
|---|---|---|---|---|---|---|
| 1. t-Butyl peroxy 2-chloro-2-methyl propionate (TBPCMPr) | 194.65 | 8.22 | 7.70 | 93.7 | 14.30/17.95 | 74.6 |
| 2. t-Amyl peroxy 2-chloro-2-methyl propionate (TAPCMPr) | 208.55 | 7.67 | 7.50 | 97.8 | 23.27/29.58 | 76.9 |
| 3. t-Butyl peroxy 2-chloro-2-methyl pentanoate (TBPCMPe) | 222.61 | 7.19 | 6.56 | 91.3 | 33.26/37.23 | 81.5 |
| 4. t-Butyl peroxy 2-chloro-2-ethyl butyrate (TBPCEB) | 222.61 | 7.19 | 6.92 | 96.3 | 10.29/13.18 | 75.2 |
| 5. t-Amyl peroxy 2-chloro-2-ethyl butyrate (TAPCEB) | 236.61 | 6.76 | 6.14 | 90.9 | 14.15/18.83 | 68.3 |
| 6. t-Butyl peroxy 2-chloro-2-ethyl hexanoate (TBPCEH) | 250.73 | 6.38 | 6.34 | 99.7 | 12.48/34.10 | 36.6 |
| 7. 2,5-Dimethyl-2,5-di(2-chloro-2-methyl pentanoyl peroxy) hexane (DM-DCMPeH) | 443.43 | 7.22 | 7.11 | 98.5 | 7.87/15.49 | 45.2 |

The following Table III illustrates the desirable half lifes obtainable with compositions of this invention:

TABLE III

HALF-LIFE DATA FOR SELECTED 2-CHLORO-2-ALKYL SUBSTITUTED PEROXYESTERS (0.2M in Benzene)

| Peroxyester | Temp, °C. | Half-Life, Hr. | 10 Hr Half-Life Temp, °C. |
|---|---|---|---|
| 1. 1,1,3,3-Tetramethyl butyl peroxy-2-chloro-2-ethyl butyrate (TMBPCEB) | 47.5 | 23.22 | |
|  | 50 | 16.84 | 54.1 |
|  | 55 | 9.00 | |
|  | 65 | 2.38 | |
| 2. TBPCEH | 55 | 11.55 | 56.2 |
|  | 65 | 3.72 | |
|  | 75 | 1.16 | |
|  | 80 | 0.68 | |

As indicated earlier, the present materials are useful for initiation of monomers having polymerizable ethylenic or vinyl unsaturation. Typical of such materials are ethylene, styrene, methyl methacrylate and vinyl chloride.

To illustrate the utility as initiators in vinyl chloride polymerizations, each of the peroxyesters listed in Table II was utilized as an initiator according to the following procedure:

The suspension polymerizations were performed in pop bottles using uninhibited monomer at 70° C. in a constant temperature bath. Duplicate bottles were analyzed at each polymerization time interval. Bottles were frozen before venting-off excess monomer. The following table lists some general information about the polymerization procedure used:

| Bottle Size, fl. oz. | Bath Mixing Speed, RPM | H$_2$O/VCM Ratio | Amt. Suspension Agent/100 g. VCM |
|---|---|---|---|
| 6 | 42 | 2.5 | 0.30g Dow Methocel K35, 35 cps |

Results are shown in Table IV. t-Butyl peroxy 2-chloro-2-methyl propionate (TBPCMPr) was included for comparison as representative of known compounds with shorter aliphatic chains attached to the alpha carbon relative to the carbonyl, i.e., peroxyesters having 8 or less carbon atoms. As the results of Table IV indicate, the peroxyesters, particularly the more comparable monoperoxyesters, of the present invention are more efficient on an equal molar basis when compared with TBPCMPr.

TABLE IV

COMPARISON OF VINYL CHLORIDE POLYMERIZATIONS WITH VARIOUS 2-CHLORO-2-ALKYL SUBSTITUTED PEROXYESTERS AT 70° C.

| Peroxyester | % Wt. Used | Moles (× 10$^{-4}$) /100g VCM | Time, Hrs. | % Conversion 1.5 | 3.5 | 5.0 |
|---|---|---|---|---|---|---|
| 1. TBPCMPr | 0.039 | 2.0 | | — | — | 36.5[1] |
| 2. TAPCMPr | 0.042 | 2.0 | | — | — | 40.9[2] |
| 3. TBPCMPe | 0.0445 | 2.0 | | — | — | 64.3[2] |
| 4. TBPCEB | 0.0445 | 2.0 | | — | — | 73.9 |
| 5. TAPCEB | 0.047 | 2.0 | | — | — | 76.5 |
| 6. TBPCEH | 0.05 | 2.0 | | — | — | 76.4[3] |
|  | 0.055 | 2.2 | | 14.6[4] | 52.3 | 81.1[2] |
| 7. TMBPCEB | 0.06 | 2.2 | | 22.5[4] | 64.0 | 79.9[2] |
| 8. DM-DCMPeH | 0.08 | 1.8 | | 26.3 | 79.1 | 90.0 |
|  | 0.097 | 2.2 | | — | — | 91.5 |
| 9. DM-DCMPrH | 0.084 | 2.2 | | — | — | 45.2 |

[1]Average value from 3 runs
[2]Average value from 2 runs
[3]Average value from 4 runs
[4]Single bottle value Aside from the selection of the peroxyester having the structure discussed above, the practice of the present method in polymerizations involving one or more monomers, such as that of styrene, vinyl chloride, vinyl acetate, and ethylene, is consistent with prior art procedures for initiating the polymerization of such monomers. Thus, the present peroxyesters are added in amounts generally comparable to those of peresters previously used and will usually fall within the range of about 0.005% to 3% by weight of the monomer content and more commonly about 0.01–0.5% by weight of the monomer content. For practical purposes the minimum amount of the peroxyester is added which will effectively initiate the polymerization of the monomer mass. The usual conditions of temperature, pressure, solvents, and the like used in the polymerization of these monomers may be employed. In addition, it is contemplated that co-catalysts may be included to initiate the polymerization.

Table V shows results typical of the performance of peroxyesters of the present invention for efficient curing of unsaturated polyester resins.

It is divided into three sets because of the number of peroxyesters tested. Two peroxides were used in all three sets: t-butyl peroxy 2-chloro-2-ethyl hexanoate and benzyol peroxide. t-Butyl peroxy 2-chloro-2-methyl propionate (TBPCMPr) was used in both sets 1 and 2; again, for comparison to the monoperoxyesters of the present invention. TBPCMPr is the first entry in both sets 1 and 2. The peroxyesters of the present invention are superior to TBPCMPr because they cure faster at lower molar levels. Although there is a shift in gel times between the three sets, the relationship of TMPCMPr to either TBPCEH or BZP in sets 1 and 2 is constant and the relationship of TBPCEH to BZP in all three sets is constant.

TABLE V

HOT BLOCK GEL TESTS WITH POLYESTER RESIN USING VARIOUS 2-CHLORO-2-ALKYL SUBSTITUTED PEROXYESTERS[1]

Resin: USS Chemical MR-941 (Isophthalic)
Block Temp: 180 ± 1° F. (82° C.)
1% wt of each peroxide (100% purity basis)

| Peroxide | Moles Peroxide ($\times 10^{-3}$)/100g Resin | Gel Time, Min. | Exotherm Time, Min. | Peak Temp, °F. |
|---|---|---|---|---|
| SET 1 | | | | |
| 1. TBPCMPr | 5.15 | 6'44" | 7'44" | 259 |
| 2. TAPCMPr | 4.8 | 5'41" | 6'29" | 262 |
| 3. TBPCMPe | 4.5 | 5'34" | 6'22" | 254 |
| 4. TBPCEH | 4.0 | 4'15" | 5'2" | 260 |
| 5. Benzoyl Peroxide (BZP) | — | 9'33" | 10'48" | 248 |
| SET 2 | | | | |
| 1. TBPCMPr | 5.15 | 6'17" | 7'13" | 268 |
| 2. TBPCEB | 4.5 | 3'45" | 4'30" | 266 |
| 3. TAPCEB | 4.25 | 3'15" | 3'53" | 264 |
| 4. TBPCEH | 4.0 | 3'48" | 4'32" | 269 |
| 5. BZP | — | 9'2" | 10'14" | 251 |
| SET 3 | | | | |
| 1. TBPCEH | 4.0 | 2'48" | 3'24" | 264 |
| 2. TMBPCEB | 3.6 | 1'58" | 2'28" | 263 |
| 3. DM-DCMPeH | — | 2'37" | 3'12" | 263 |
| 4. DM-DCMPrH | — | 2'41" | 3'25" | 255 |
| 5. BZP | — | 6'31" | 7'33" | 252 |

[1] 5cc of 50g mixture charged to Hot Block

Aside from the employment of the novel compounds of the present invention, the practice of the instant method in curing of polyester resins is consistent with known procedures.

The unsaturated polyester resins cured by the present process comprise a linear or only slightly branched polyester resin and a peroxide cross-linkable monomeric compound. The linear or slightly branched polyester resin is typically prepared as a condensation or reaction product of an unsaturated polybasic and a polyhydric compound; for example, the condensation product of an unsaturated dibasic acid of alpha-beta ethylenic unsaturation and a di or trihydric compound, such as a glycol. Often a saturated polybasic acid or anhydride, such as a dibasic acid, is employed with the unsaturated acid or anhydride to modify the reactivity of the unsaturated resin.

Examples of typical polyhydric alcohols include, but are not limited to: ethylene glycol; 1,2-propane diol; 1,3-propane diol; diethylene glycol; dipropylene glycol; triethylene glycol; tripropylene glycol; 1,2-butane diol; 1,3-butane diol; 1,4-butane diol; neopentyl glycol; 2,2,5-trimethylpentane diol; cyclohexanedimethanol; dibromoneopentyl glycol; dibromobutane diol; trimethylolpropane; pentaerythritol; trimethylpentane diol; dipropoxy adducts of bis phenol A; and dipropoxy adducts of hydrogenated bis phenol A.

Examples of saturated polybasic acids include, but are not limited to: isophthalic acid; orthophthalic acid; terephthalic acid; tetrabromophthalic acid; tetrachlorophthalic acid; tetrahydrophthalic acid; adipic acid; succinic acid; azelaic acid; glutaric acid; nadic acid and the various anhydrides obtained therefrom.

Examples of unsaturated polybasic acids include, but are not limited to: maleic acid; fumaric acid; itaconic acid; citraconic acid and anhydrides obtained therefrom.

Examples of peroxide curable cross-linking monomers employed with the linear polyesters include, but are not limited to: styrene, vinyl toluene; acrylates and methacrylates like methylmethacrylate; alphamethyl styrene; chloro styrene; and diallyl phthalate. The liquid unsaturated polyester resins also typically contain small amounts of inhibitors in order to prevent premature reaction, such as, for example: hydroquinone; quinone and tertiary butyl catechol. These monomers, together with the linear polyesters may be admixed together in various proportions as is known in the art in order to obtain resins with varying properties, in amounts of about 1 to 60% by weight; typically, for example, 5 to 45%. Such liquid resin compositions may include a wide variety of other additives to include: viscosity index improvers; rheological agents; flame retardants; thermoplastic polymers; fillers such as hollow glass or plastic microsphere beads; wood flour; silica; diatomaceous earth; pigments; dyes, stabilizers; glass fibers; release agents; extenders; catalysts; alumina surfactants; and other additives (see, for example, compounds in "Unsaturated Polyester", Modern Plastics Encyclopedia, Volume 50, No. 10a, 1973–1974, pp. 66–68, hereby incorporated by reference).

The components of the polyester resins may be varied as is known in the art to impart the desired properties to the cured resin. Typically, flexible resins employ greater amounts of adipates or azeleates, while more rigid resins use phthalates, both with a variety of different glycols.

Although the foregoing invention has been described in some detail by way of illustration and example for purposes of clarity of understanding, it is understood that certain changes and modifications may be practiced within the spirit of the invention as limited only by the scope of the appended claims.

What is claimed is:

1. In the polymerization of a monomer mass selected from the group consisting of ethylene, styrene, methyl methacrylate and vinyl chloride and in the copolymerizations thereof, including copolymerization with vinyl acetate, the improvement in which the polymerization and copolymerization of said monomer mass is initiated with a peroxyester of the formula:

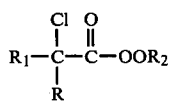

wherein $R_2$ is selected from

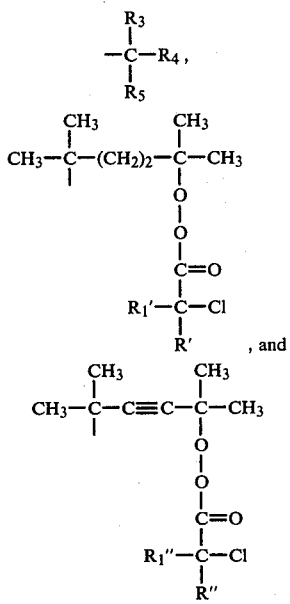

and R and $R_1$ are alkyl groups which collectively contain up to about 10 carbon atoms providing $R_1$ and R are not both methyl when $R_2$ is t-butyl, $R'$ and $R_1'$ are alkyl groups which collectively contain up to about 10 carbon atoms, $R''$ and $R_1''$ are alkyl groups which collectively contain up to about 10 carbon atoms, and $R_3$, $R_4$ and $R_5$ are alkyl groups which collectively contain up to about 9 carbon atoms.

2. A method according to claim 1 wherein $R_2$ is alkyl of the formula:

and $R_3$, $R_4$, and $R_5$ are alkyl groups which collectively contain from 3 to about 9 carbon atoms.

3. A method according to claim 1 wherein $R_3$, $R_4$, and $R_5$ collectively contain from 3 to 6 atoms.

4. A method according to claim 1 wherein R and $R_1$ have from 2 to about 7 carbon atoms.

5. A method according to claim 1 wherein $R_3$ and $R_5$ are each methyl and $R_4$ is methyl or ethyl.

6. A method according to claim 1 wherein R is methyl or ethyl and $R_1$ is from 1 to 5 carbon atoms.

7. A method according to claim 1 wherein $R_2$ has the formula:

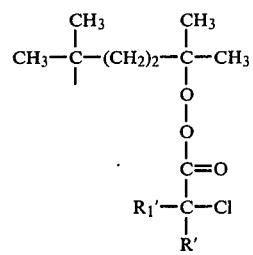

and $R_1'$ and $R'$ are alkyl groups which collectively contain up to about 10 carbon atoms.

8. A method according to claim 1 wherein $R_1'$ and $R'$ collectively contain from about 2 to about 7 carbon atoms.

9. A method according to claim 1 wherein R and $R_1$ have from about 2 to about 7 carbon atoms.

10. A method according to claim 1 wherein $R_1$ is the same as $R_1'$ and $R'$ is the same as R.

11. A method according to claim 1 wherein $R_2$ is of the formula:

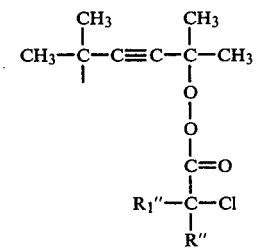

wherein $R_1''$ and $R''$ collectively have from about 2 to about 10 carbon atoms.

12. A method according to claim 1 wherein $R_1''$ and $R''$ collectively have from 2 to 7 carbon atoms.

13. A method according to claim 1 wherein $R_1$ and R collectively have from about 2 to about 7 carbon atoms.

14. A method according to claim 1 wherein $R_1$ is the same as $R_1''$ and $R''$ is the same as R.

15. A method in accordance with claim 1 wherein said peroxyester is t-amyl peroxy 2-chloro-2-methyl propionate.

16. A method in accordance with claim 1 wherein said peroxyester is t-butyl peroxy-2-chloro-2-methyl pentanoate.

17. A method in accordance with claim 1 wherein said peroxyester is t-butyl peroxy-2-chloro-2-ethyl butyrate.

18. A method in accordance with claim 1 wherein said peroxyester is t-amyl peroxy-2-chloro-2-ethyl butyrate.

19. A method in accordance with claim 1 wherein said peroxyester is t-butyl peroxy 2-chloro-2-ethyl hexanoate.

20. A method in accordance with claim 1 wherein said peroxyester is 2,5-dimethyl-2,5-di (2-chloro-2-methyl pentanoyl peroxy) hexane.

21. A method in accordance with claim 1 wherein said peroxyester is 2,5-dimethyl-2,5-di (2-chloro-2-methyl propionyl peroxy) hexyne-3.

22. A polymerization according to claim 1 wherein said monomer mass is vinyl chloride.

* * * * *